United States Patent
Beck et al.

(10) Patent No.: US 11,730,704 B2
(45) Date of Patent: Aug. 22, 2023

(54) LUTEIN COMPOSITION SUITABLE FOR INFANT FOOD FORMULATIONS

(71) Applicant: DSM IP ASSETS B.V., Heerlen (NL)

(72) Inventors: Markus Beck, Basel (CH); Andrea Hitzfeld, Basel (CH); Bernd Schlegel, Basel (CH); Christian Schaefer, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/780,244

(22) PCT Filed: Mar. 27, 2014

(86) PCT No.: PCT/EP2014/056126
§ 371 (c)(1),
(2) Date: Sep. 25, 2015

(87) PCT Pub. No.: WO2014/154788
PCT Pub. Date: Oct. 2, 2014

(65) Prior Publication Data
US 2016/0038436 A1    Feb. 11, 2016

(30) Foreign Application Priority Data

Mar. 28, 2013 (EP) .................... 13161534

(51) Int. Cl.
| | | |
|---|---|---|
| A61K 31/047 | (2006.01) | |
| A23L 33/00 | (2016.01) | |
| A23P 10/40 | (2016.01) | |
| A23L 33/10 | (2016.01) | |
| A61K 9/00 | (2006.01) | |
| A61K 9/16 | (2006.01) | |

(52) U.S. Cl.
CPC ............ *A61K 31/047* (2013.01); *A23L 33/10* (2016.08); *A23L 33/40* (2016.08); *A23P 10/40* (2016.08); *A61K 9/0095* (2013.01); *A61K 9/16* (2013.01); *A23V 2002/00* (2013.01)

(58) Field of Classification Search
CPC ....................................................... A23L 33/10
See application file for complete search history.

(56) References Cited

U.S. PATENT DOCUMENTS 7,829,126 B2 * 11/2010 Barrett-Reis ........... A23L 33/12
                                                            426/72
2003/0228392 A1   12/2003  Zimmer 2008/0241320 A1   10/2008  Schafer et al.
2010/0069510 A1    3/2010  Schafer et al.
2011/0129573 A1    6/2011  Albrecht et al.

FOREIGN PATENT DOCUMENTS

| CN | 1610662 | 4/2005 |
|---|---|---|
| CN | 101212910 | 7/2008 |
| CN | 101219125 | 7/2008 |
| CN | 101610683 | 12/2009 |
| CN | 101626695 | 1/2010 |
| CN | 101902922 | 12/2010 |
| CN | 101 856 046 | 4/2012 |
| CN | 102784600 | 11/2012 |
| EP | 1 967 081 | 9/2008 |
| JP | 2005-512587 | 5/2005 |
| JP | 2009-512657 | 3/2009 |
| WO | WO 2004/084862 | 10/2004 |
| WO | WO 2008/098694 | * 8/2008 |
| WO | WO 2008/107152 | 9/2008 |
| WO | WO 2009/080702 | 7/2009 |
| WO | WO 2010/149759 | 12/2010 |
| WO | WO 2012/069322 | 5/2012 |
| WO | WO 2012/139895 | 10/2012 |

OTHER PUBLICATIONS

Capeding et al., "Research Lutein-fortified infant formula fed to healthy term infants: evaluation of growth effects and safety"—Nutrition Journal, 2010, 9:22, pp. 1-9. (Year: 2010).*
International Search Report for PCT/EP2014/056126, dated Apr. 17, 2014, 4 pages.
Office Action issued in PH Appln. No. 1/2015/502242 dated Oct. 1, 2018.
DSM Nutritional Products Ltd., Product Information Composition, FloraGLO® Lutein 1% SD/S, Version 2 (Mar. 5, 2020).
DSM Nutritional Products Ltd., Product Information Composition, FloraGLO® Lutein 5% CWS/S-TG, Version 2 (Apr. 30, 2018).
DSM Nutritional Products Ltd., Product Information Composition, FloraGLO® Lutein 20 % SAF, (Nov. 29, 2012).
Translation of Office Action issued in CN Appln. No. 201810056977.3 dated Nov. 30, 2020, 20 pages.
Office Action issued in CN Appln. No. 201810056977.3 dated Nov. 30, 2020.
Office Action issued in KR Appln. No. 10-2015-7030183 dated Aug. 24, 2020 (w/ translation).
K. Dhanalakshmi et al.,"Agglomeration of Food Powder and Applications," Critical Reviews in Food Science and Nutrition 2011, 51, 432-441.

* cited by examiner

*Primary Examiner* — Elizabeth Gwartney
(74) *Attorney, Agent, or Firm* — Nixon & Vanderhye P.C.

(57) ABSTRACT

The present invention is related to a powderous composition which comprises lutein and which is used in infant food formulations or premixes for infant food formulations.

7 Claims, No Drawings

LUTEIN COMPOSITION SUITABLE FOR INFANT FOOD FORMULATIONS

This application is the U.S. national phase of International Application No. PCT/EP2014/056126 filed 27 Mar. 2014, which designated the U.S. and claims priority to EP Patent Application No. 13161534.6 filed 28 Mar. 2013, the entire contents of each of which are hereby incorporated by reference.

The present invention is related to a powderous composition which comprises lutein and which is used in infant food formulations or premixes for infant food formulations.

Lutein which has the following formula

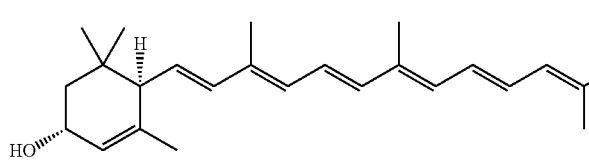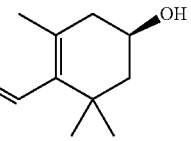

is obtained usually from plants or eggs.

It can also be synthesized chemically.

Due to the C—C double bonds lutein can have various stereochemical isomers (E/Z forms). In the context of the present invention the different isomers do not have an essential effect. The term "lutein" always covers all stereochemical isomers.

It was found that lutein plays a vital role in eye health. The hypothesis for the natural concentration is that lutein helps keep the eyes safe from oxidative stress and the high-energy photons of blue light. Various research studies have shown that a direct relationship exists between lutein intake and pigmentation in the eye.

For that reason lutein is also an important ingredient in the diet for infants (Age 0-6).

Therefore, the goal of the present invention was to provide a composition which comprises lutein and which has excellent properties as such as well as allows to produce a (infant food) formulation comprising such a composition, which has also excellent properties.

It was found that a powderous composition comprising particles having (a) an inner phase, which comprises lutein, and (b) a matrix, which comprises at least one hydrocolloid, characterized in that (i) the inner phase has an average size D [3,2] of less than 30 μm, and (ii) the particle has an average size D [3,2] of 10-150 μm, and wherein the inner phase is always smaller than the particle, does show improved properties.

All the sizes of the inner phase D [3,2] as well as of the particles D [3,2] in the context of the present patent application were determined by using a Mastersizer 2000. The particle size of the inner phase was determined after redispersing the powderous composition in water, whereas the powderous particles of the composition were determined as such.

The composition according to the present invention is used in infant food formulations or in premixes (which are then used to produce infant food formulations). The premix is usually in a dry form. The premix is usually produced by mixing the composition according to the present invention with other suitable ingredients, which are useful and/or essential in an infant formulation and/or premix (or which are useful and/or essential for the production of an infant formulation and/or premix).

The infant formulation in the context of the present invention is usually a dry formutation, which is then dissolved either in water or in milk.

Dry means that the water content is less than 5 weight-% (wt-%), based on the total weight of the composition, premix or formulation.

The advantages of the composition according to the present invention are:

the composition is storage stable no colored (red) spots in the infant food formulation no bleeding when the composition is blended to premix and/or an infant food formulation no color formation, when the infant food formulation is dissolved in water (or milk).

Preferably the inner phase has an average size D [3,2] of 0.1 μm to 30 μm.

Preferably the inner phase has an average size D [3,2] of 0.2 μm to 20 μm.

Hydrocolloids are hydrophilic polymers, of vegetable, animal, microbial or synthetic origin, that generally contain many hydroxyl groups and may be polyelectrolytes.

A hydrocolloid is defined as a colloid system wherein the colloid particles are hydrophilic polymers dispersed in water. A hydrocolloid has colloid particles spread throughout water, and depending on the quantity of water available that can take place in different states, e.g., gel or sol (liquid). Hydrocolloids can be either irreversible (single-state) or reversible.

The hydrocolloids are preferably chosen from the group consisting of modified polysaccharides, maltodextrin, glucose syrup and gums.

The term "modified polysaccharide" as used in the present specification and claims refers to a polysaccharide which has been modified by known methods (chemically or physically, including enzymatic or thermal reactions) to be a good protective hydrocolloid for the stabilization of lipophilic surfaces in a fine dispersion in the aqueous medium. Accordingly, the modified polysaccharide has been modified to have a chemical structure which provides it with a hydrophilic (affinity to water) portion and a lipophilic (affinity to dispersed phase) portion. This enables it to dissolve in the dispersed lipophilic phase and in the continuous water phase. Preferably the modified polysaccharide has a long hydrocarbon chain as part of its structure (preferably $C_{5-18}$).

Modified polysaccharides are well known materials which are available commercially, or may be prepared by a skilled person using conventional methods. A preferred modified polysaccharide is modified starch. Modified starches are made from starches substituted by known chemical methods with hydrophobic moieties. For example starch may be treated with cyclic dicarboxylic acid anhydrides such as succinic anhydrides, substituted with a hydrocarbon chain (see Modified Starches: Properties and Uses, ed. O. B. Wurzburg, CRC Press, Inc., Boca Raton, Fla. (1991)). A particularly preferred modified starch of this invention has the following structure (I)

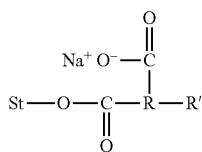

wherein St is a starch, R is an alkylene group and R' is a hydrophobic group.

Preferably the alkylene group is a lower alkylene group, such as dimethylene or trimethylene. R' may be an alkyl or alkenyl group, preferably $C_5$ to $C_{18}$. A preferred compound of Formula I is starch sodium octenyl succinate. It is available commercially from, among other sources, Ingredion Inc., as Capsule and Hicap®. Making this compound, and compounds of Formula I in general, is known in the art (see Modified Starches: Properties and Uses, ed. O. B. Wurzburg, CRC Press, Inc., Boca Raton, Fla. (1991)).

Glucose syrup is a food syrup, made from the hydrolysis of starch.

A preferred gum in the context of the present invention is gum Arabic (=gum *acacia*).

The powderous composition according to the present invention comprises
  (a) 0.01-30 wt-%, based on the total weight of the composition, of lutein, and
  (b) 70-99.99 wt-%, based on the total weight of the composition, of at least one hydrocolloid, and
  (c) optionally up to 25 wt-%, based on the total weight of the composition, of at least one auxiliary agent.

It is clear that all the percentages always add up to 100.

A preferred powderous composition according to the present invention comprises
  (a) 0.1-15 wt-% based on the total weight of the composition, of lutein and
  (b) 70-90 wt-%, based on the total weight of the composition, of at least one hydrocolloid and
  (c) 15-25 wt-%, based on the total weight of the composition, of at least one auxiliary agent.

A preferred powderous composition according to the present invention comprises
  (a) 0.2-10 wt-% based on the total weight of the composition, of lutein and
  (b) 75-90 wt-%, based on the total weight of the composition, of at least one hydrocolloid and
  (c) 15-25 wt-%, based on the total weight of the composition, of at least one auxiliary agent.

These powderous compositions are dry but they could contain some water (less than 5 wt-%, based on the total weight of the composition, usually less than 3 wt-%).

The auxiliary agents can be any commonly known excipients, which are
  useful for the composition and/or the premix and/or the infant food formulation and/or
  useful for the production of the composition and/or of the premix and/or of the infant food formulation.

Such auxiliary agents are for example antioxidants (such as ascorbic acid or salts thereof, tocopherols (synthetic or natural); butylated hydroxytoluene (BHT); butylat-ed hydroxyanisole (BHA); propyl gallate; tert. butyl hydroxyquinoline and/or ascorbic acid esters of a fatty acid); ethoxyquin, plasticisers, stabilisers, humectants (such as glycerine, sorbitol, polyethylene glycol), dyes, fragrances, fillers and buffers.

Examples are i.e. sugar (saccharides), sodium ascorbate.

The hydrocolloids are preferably chosen from the group consisting of modified polysaccharides, maltodextrin, glucose syrup and gums, and especially OSA-starch, maltodextrin and glycose syrup.

The composition according to the present invention is produced by using methods known from the prior art.

Usually the composition according to the present invention is produced by:
  first preparing the water phase which comprises
    a) the hydrocolloid or a mixture of hydrocolloids, and
    b) optionally at least one auxiliary agent, such as sugar and/or sodium ascorbate, and
    c) water
by mixing the ingredients (in any sequence) into the water (usually under stirring) and at ambient temperature.

Afterwards this phase is heated up (to a temperature of between 40 and 90° C.). Then the lutein is added (still at elevated temperature) under vigorous dispersing, which is optionally followed by a homogenizing process.

Finally the suspension is dried by a method commonly used, such as spray drying.

The powderous compositions according to the present invention are used in infant food formulations and/or in premixes for infant food formulations.

By the term infant food formulations in the context of the present invention, dry formulations are meant (especially baby milk formulations), which are then dissolved in a suitable solvent (usually water or milk, preferably water) and the dissolved form (warm or cold) is then consumed by the infant.

The infant food formulation can be in any dry form, such powder, granules as well as tablets.

A preferred infant food formulation is a dry baby milk formulation (powder, granule as or tablets) wherein the powderous composition according the present invention is incorporated (lutein fortified baby milk formulation).

Therefore the powderous composition according to the present invention can added as such to all other ingredients to produce an infant food formulation; or the powderous composition according to the present invention can be mixed with other ingredients for an infant food formulation, which is called a premix. This premix is then used to produce an infant food formulation.

Therefore a further embodiment of the present invention is a process of production of a dry premix and/or a dry infant food formulation comprising at least one powderous composition as described above.

The amount of the powderous composition according to the present invention in such a premix and/or infant food formulation can vary.

The concentration of lutein is usually not more than 0.25 ppm in the liquid infant food formulation (dry infant food formulation dissolved in milk or preferably in water).

Therefore a further embodiment of the present invention is a dry premix and/or a dry infant food formulation comprising at least one powderous composition as described above.

The following examples serve to illustrate the invention. The percentages are expressed in weight percentages and the temperatures are degrees Celsius, if not otherwise defined.

EXAMPLES

Example 1

408.5 g Maltodextrin and 432.2. g HiCap IMF and 210.7 g Glucidex 28 E were added to 600 g distilled water. The mixture was stirred and after a few minutes the mixture was heated to about 60° C. After 20 minutes 10.8 g sodium ascorbate was added under stirring. 10 minutes later 9.6 g lutein was added and the mixture was vigorously dispersed.

Afterwards the suspension was spray dried.

The following table shows the amounts of the various ingredients after spray drying:

| Ingredients | Amount [wt-%] |
|---|---|
| Lutein | 1.2 |
| HiCap IMF | 40.2 |
| Maltodextrin | 38.0 |
| Glucidex 28 E | 19.6 |
| Na-Ascorbate | 1.0 |

The average size of the inner phase D[3,2] was 3.19 μm and the average particles size was 45.92 μm.

Example 2

The same process as in Example 1 was repeated but instead of Glucidex 28 E sugar was used.

The following table shows the amounts of the various ingredients after spray drying:

| Ingredients | Amount [wt-%] |
|---|---|
| Lutein | 1.2 |
| HiCap IMF | 40.2 |
| Maltodextrin | 38.0 |
| Sugar | 19.6 |
| Na-Ascorbate | 1.0 |

The average size of the inner phase D[3,2] was 3.02 μm and the average particles size was 81.82 μm.

Both compositions did not bleed when added to a premix or a infant food formulation. Furthermore, no color formation was observed when the infant food formulation (baby milk powder) comprising one of these compositions were dissolved in water.

Example 3

Baby Milk Powder Comprising Composition of Example 1

The composition of Example 1 was used adding to a baby milk powder formulation. 0.83 g of the powderous composition of Example 1 were incorporating (by mixing).

The following table shows the list of ingredients of the lutein fortified baby milk powder:

| Ingredients | unit | Content per 100 g powder | Content per 100 ml serving |
|---|---|---|---|
| Protein | g | 9.20 | 1.4 |
| Carbohydrates | g | 53.2 | 8.1 |
| Fat | g | 23 | 3.5 |
| Sodium | g | 0.13 | 0.02 |
| Potassium | mg | 493 | 75 |
| Calcium | mg | 348 | 53 |
| Phosphorus | mg | 197 | 30 |
| Chloride | mg | 276 | 42 |
| Magnesium | mg | 32.2 | 4.9 |
| Iron | mg | 4.60 | 0.7 |
| Zinc | μg | 3.3 | 0.5 |
| Copper | μg | 263 | 40 |
| Iodine | μg | 65 | 9.9 |
| Manganese | μg | 46 | 7 |
| Selenium | μg | 9.85 | 1.5 |
| Fluorid | μg | 38.8 | 5.9 |
| Vitamin C | mg | 67.7 | 10.3 |
| Vitamin A | μg | 460 | 70 |
| Vitamin D | μg | 7.88 | 1.2 |
| Vitamin E | μg | 4.6 | 0.7 |
| Vitamin B1 | μg | 394 | 60 |
| Vitamin B2 | μg | 834 | 127 |
| Vitamin B6 | μg | 263 | 40 |
| Vitamin B12 | μg | 1 | 0.15 |
| Folic acid | μg | 67.7 | 10.3 |
| Pantotenic acid | μg | 3258 | 496 |
| Vitamin K | μg | 32.2 | 4.9 |
| Biotin | μg | 10.51 | 1.6 |
| Niacin | μg | 2621 | 399 |
| Choline | mg | 99.2 | 15.1 |
| Inositol | mg | 32.2 | 4.9 |
| Lutein | μg | 1000 | 152 |

This lutein fortified baby milk powder showed excellent storage stability. No bleeding was observed during and after the addition of the composition of Example 1. No colored (red) spots have been seen in the fortified baby milk powder. Furthermore the baby milk powder shows excellent dissolving properties in water (dissolves fast) and no color change of the dissolved baby milk formulation.

Example 4

Baby Milk Powder Comprising Composition of Example 1

For this baby milk formulation a lower concentration of the composition of Example 1 was added (all the other ingredients are the same in the same concentration)

| Ingredients | unit | Content per 100 g powder | Content per 100 ml serving |
|---|---|---|---|
| Protein | g | 9.20 | 1.4 |
| Carbohydrates | g | 53.2 | 8.1 |
| Fat | g | 23 | 3.5 |
| Sodium | g | 0.13 | 0.02 |
| Potassium | mg | 493 | 75 |
| Calcium | mg | 348 | 53 |
| Phosphorus | mg | 197 | 30 |
| Chloride | mg | 276 | 42 |
| Magnesium | mg | 32.2 | 4.9 |
| Iron | mg | 4.60 | 0.7 |
| Zinc | μg | 3.3 | 0.5 |
| Copper | μg | 263 | 40 |
| Iodine | μg | 65 | 9.9 |
| Manganese | μg | 46 | 7 |
| Selenium | μg | 9.85 | 1.5 |
| Fluorid | μg | 38.8 | 5.9 |
| Vitamin C | mg | 67.7 | 10.3 |
| Vitamin A | μg | 460 | 70 |

-continued

| Ingredients | unit | Content per 100 g powder | Content per 100 ml serving |
|---|---|---|---|
| Vitamin D | μg | 7.88 | 1.2 |
| Vitamin E | μg | 4.6 | 0.7 |
| Vitamin B1 | μg | 394 | 60 |
| Vitamin B2 | μg | 834 | 127 |
| Vitamin B6 | μg | 263 | 40 |
| Vitamin B12 | μg | 1 | 0.15 |
| Folic acid | μg | 67.7 | 10.3 |
| Pantotenic acid | μg | 3258 | 496 |
| Vitamin K | μg | 32.2 | 4.9 |
| Biotin | μg | 10.51 | 1.6 |
| Niacin | μg | 2621 | 399 |
| Choline | mg | 99.2 | 15.1 |
| Inositol | mg | 32.2 | 4.9 |
| Lutein | μg | 164 | 25 |

Also this lutein fortified baby milk powder showed excellent storage stability. No bleeding was observed during and after the addition of the composition of Example 1. No colored (red) spots have been seen in the fortified baby milk powder. Furthermore the baby milk powder shows excellent dissolving properties in water (dissolves fast) and no color change of the dissolved baby milk formulation.

The invention claimed is:

1. An infant food formulation or premix thereof comprising a powderous composition of spray-dried particles, wherein each of the particles comprise, based on the total weight of the powderous composition:
   (A) 78.2 wt. % of a hydrocolloid mixture comprising 40.2 wt. % of an OSA starch together with 38.0 wt. % of either glucose syrup or maltodextrin;
   (B) 1.2 wt. %, of lutein in an inner phase of the particle, and
   (C) 19.6 wt. % of sugar as an auxiliary agent, wherein the inner phase of each of the spray-dried particles has an average size D[3,2] of 3.02 μm to 30 μm,
   the particles have an average size D [3,2] of 10 μm-150 μm, and
   the inner phase of a particle is always smaller than the particle having that inner phase.

2. The infant food formulation or premix according to claim 1, wherein the inner phase of each of the spray-dried particles has an average size D[3,2] of 3.19 μm to 30 μm.

3. The infant food formulation or premix according to claim 1, wherein the inner phase of each of the spray-dried particles has an average size D[3,2] of 3.02 μm to 20 μm.

4. The infant food formulation or premix according to claim 1, which comprises at least one additional auxiliary agent which is selected from the group consisting of antioxidants, plasticisers, stabilisers, humectants, dyes, fragrances, filler and buffers.

5. The infant food formulation or premix according to claim 4, wherein the antioxidants are selected from the group consisting of butylated hydroxytoluene (BHT), butylated hydroxyanisole (BHA), propyl gallate, tert. butyl hydroxyquinoline, ascorbic acid esters of a fatty acid, ethoxyquin, synthetic tocopherols and natural tocopherols.

6. The infant food formulation or premix according to claim 4, wherein the antioxidants are selected from the group consisting of ascorbic acid or salts thereof, synthetic tocopherols and natural tocopherols.

7. The infant food formulation or premix according to claim 4, wherein the humectants are selected from the group consisting of glycerine, sorbitol and polyethylene glycol.

\* \* \* \* \*